United States Patent [19]
Sarin et al.

[11] Patent Number: 6,002,060
[45] Date of Patent: Dec. 14, 1999

[54] PROCESS FOR OLIGOMERISATION OF ALPHA-OLEFINS

[76] Inventors: Rakesh Sarin, House No. 2204, Sector-9, Faridabad; Sabyasachi Sinha Ray, House No. B-65, Sarita Vihar, New Delhi; Deepak Kumar Tuli, House No. 866, Sector-9, Faridabad; Madan Mohan Rai, House No. 866, Sector-15, Faridabad; Sobhan Ghosh, House No. 188, Sector-14, Faridabad; Akhilesh Kumar Bhatnagar, House No. 205, Sector-7A, Faridabad; Swaminathan Sivaram, C-II/2, NCL Colony, Pune; Thekke Pangil Mohandas, B-104, Ashit Apartments, Sudhir Pawar Path, Modi Baug, Pune; Dattatraya Haribhau Gholap, E-28, NCL Colony, Pune; Mallinamadugu Jogimarappa Gari Yanjarappa, New Hostel, NCL, Pune, all of India

[21] Appl. No.: 09/064,177

[22] Filed: Apr. 22, 1998

[51] Int. Cl.$^6$ ..................................................... C07C 2/02
[52] U.S. Cl. ............................................. 585/522; 585/520
[58] Field of Search ...................................... 585/520, 522

[56] References Cited

U.S. PATENT DOCUMENTS

| | | | |
|---|---|---|---|
| 4,579,991 | 4/1986 | White ...................................... | 585/522 |
| 4,822,945 | 4/1989 | Bronstert et al. ....................... | 585/522 |
| 4,835,331 | 5/1989 | Hammershaimb et al. ............ | 585/520 |
| 5,177,276 | 1/1993 | Beach et al. ........................... | 585/522 |

*Primary Examiner*—Walter D. Griffin
*Assistant Examiner*—In Suk Bullock
*Attorney, Agent, or Firm*—Venable; George H. Spencer; Charles C.P. Rories

[57] ABSTRACT

A process for the oligomerization and co-oligomerization of alpha olefins by subjecting olefins to the step of oligomerization in the presence of a supported aluminum chloride catalyst and an organoaluminum compound as a promoter. The catalyst is separated and the reaction product is subjected to the step of fractional distillation for removal of the solvent. The oligomers are further fractionated to obtain poly alpha olefins.

13 Claims, No Drawings

PROCESS FOR OLIGOMERISATION OF ALPHA-OLEFINS

FIELD OF INVENTION

This invention relates to an improved process for oligomerization and co-oligomerization of α olefins. More particularly, it relates to the process of oligomerization and co-oligomerization using a solid catalyst capable of giving olefin oligomers and co-oligomers with high catalyst activity especially over a wide temperature range.

The alpha olefins suitable for use in the process have the general formula $C_nH_{2n}$ where n is an integer between 4 and 20. The resulting polyalpha-olefins are useful as synthetic lubricating oils.

PRIOR ART

Lewis acids like boron trifluoride and aluminum chloride are known catalysts for oligomerization of higher alpha olefins (U.S. Pat. Nos. 3,382,291; 3,763,244;). However, quantitative conversion of olefins can be achieved by using these catalysts only when the catalyst concentration reaches 2–5% by weight of olefin. This leaves a high residue of halogen in the oligomer, which is undesirable in many applications of these products.

The catalyst comprises a supported aluminum chloride-organoaluminum compound catalyst. The said catalyst consists of anhydrous aluminum chloride and an organo aluminum compound, preferably, diethylaluminum chloride, supported on a solid carrier, preferably silica.

OBJECTS OF THE INVENTION

The object of the present invention is to provide a process for oligomerization and co-oligomerization of olefins using a solid catalyst capable of showing high catalyst activity over a wide temperature range.

Another object of the present invention is to provide a process for oligomerization and co-oligomerization of alpha olefins of the general formula $C_nH_{2n}$ where n is an integer between 4 and 20 using a solid catalyst to prepare polyalpha olefins, useful as synthetic lubricating oils.

DESCRIPTION OF THE INVENTION

Accordingly, the present invention provides a process for oligomerization and co-oligomerization of alpha olefins, which comprises oligomerization of olefins in presence or absence of a hydrocarbon solvent, in the presence of a catalyst and a promoter at a temperature in the range of 60 to 180° C., preferably 125 to 175° C., at a pressure ranging from 0 to 2 bars for a period of 10 to 180 minutes, preferably 20 to 30 minutes allowing the reaction mixture to attain ambient temperature, separating the catalyst by conventional methods, fractionally distilling the reaction mixture containing the product to remove solvent if so necessary, further fractionating the product oligomers to obtain polyalpha-olefins in the desired carbon number range.

It has now been found that a relatively small percentage of aluminum chloride (0.1 to 0.5 wt % with respect to olefin) in conjunction with an organoaluminum compound supported on an inert carrier like silica effects quantitative conversion of alpha olefins to polyalpha-olefins. A combination of aluminum chloride on silica along with an organoaluminum compound offers a good balance of catalyst activity and control over distribution of oligomers in the desirable range suitable for application as synthetic lubricating oil.

The alpha olefins used in the present invention have the general chemical formula $C_nH_{2n}$ where n is an integer between 6 and 20, more preferably with a carbon number of $C_8$ to $C_{14}$ and most preferably those from $C_{10}$ to $C_{12}$. Such alpha olefins may be either single olefins or mixtures of olefins derived from various processes such as ethylene oligomerization, higher paraffin dehydrogenation or from refinery streams. The alpha olefin content in the olefin may at least be 50% by weight, the balance being internal olefins or their positional isomers.

The catalyst is selected from supported aluminum chloride catalyst. The promoter is an organoaluminum compound having general formula $AlR_3 X_{3-n}$ where R is a linear or branched alkyl group with carbon number 1 to 10, X is a halogen belonging to group VIIB of the periodic table and n has a value between 0.5 to 2, exemplified by organoaluminum compounds such as diethylaluminum chloride, dimethylaluminum chloride, diethylaluminum bromide, diethylaluminum fluoride, and ethylaluminum sesquichloride supported on a solid carrier, preferably silica.

The oligomerization reaction is conducted by using a veriety of methods. For example, the alpha olefin is mechanically agitated with the supported silica catalyst in a conventional stirred tank reactor. Alternatively the supported silica catalyst is packed in a fixed bed and the alpha olefin reactant fed over the bed at a controlled rate to provide an average residence time of 20 to 30 minutes in the temperature range 120 to 180° C.

The catalyst may be repeatedly reused several times by reactivating the catalyst by the addition of suitable quantity of organoaluminum compound as a promoter.

The product of oligomerization is then separated from the hydrocarbon solvent, if any, by a process of distillation under suitable conditions of temperature such as 160° C. and pressure, such as 50–60 mm Hg. The oligomer product mixture is subjected to a treatment with an adsorbent bed, consisting of adsorbent alumina, to remove residues of aluminum and chlorides.

The oligomer mixture, thus, obtained is subjected to hydrogenation using a suitable catalyst under 10 to 100 bar $H_2$ pressure, at 60 to 100° C. for 8 to 12 hours. The catalytic hydrogenation can use a number of catalyst, such as 10% Pd/C or Raney Ni, which are well known in the prior art. The hydrogenated oligomer mixture thus obtained can be further fractionated to produce narrower fractions of desired product characteristics.

The product oligomer obtained upon hydrogenation, results in synthetic lube stock in the viscosity range of 4 to 20 cSt. Changes in this range is effected by altering reaction parameters such as temperature of oligomerization and adjusting the fractionation conditions.

In another feature of the present invention the product lube stock obtained has a viscosity index of 140 and a pour point <−40° C.

The supported catalyst has 0.2 to 1.0% by weight of aluminum chloride and 0.4 to 4.0% by weight of organoaluminum compound.

The process of the present invention is described hereinbelow with examples which are illustrative only and should not be construed to limit the scope of the present invention in any manner.

EXAMPLE 1

100 mL of 1-decene, diluted with about 400 mL of saturated hydrocarbons (<50 ppm moisture) was taken in a one liter four neck round bottom flask. The flask was equipped with a magnetic stirrer, nitrogen inlet and outlet and a condenser assembly. Silica supported catalysts 4 g containing 5 wt. % of aluminum chloride and 30 wt. %. of diethylaluminum chloride was introduced into the flask. The contents were heated to 100° C. Oligomerization was carried out for 30 minutes. The product was filtered through a column of adsorbent alumina and the solvent distilled out at 160° C. under (50–60 mm Hg) pressure. The product composition was 16% dimer, 11.5% trimer, 16% tetramer, 16% pentamer 40% hexamer. The % conversion of 1-decene to oligomers was 99%. The product poly(1-decene) after hydrogenation had a viscosity index of 140 and a pour point of −45° C.

EXAMPLE 2

100 mL of 1-decene, diluted with about 400 mL of n-octane (<50 ppm moisture) was taken in a one liter four neck round bottom flask. The flask was equipped with a magnetic stirrer, nitrogen inlet and outlet and a condenser assembly. Silica supported catalyst, 4 g containing 5 wt. % of aluminum chloride and 30 wt. % of diethylaluminum chloride, was introduced into the flask. The contents were heated to 120° C. Oligomerization was carried out for 20 minutes. The product was filtered through a column of adsorbent alumina and the solvent distilled out at 160° C. under 50–60 mm Hg. The product composition was 25% dimer, 41% trimer, 17% tetramer, 17% pentamer and 40% hexamer. The % conversion of 1-decene to oligomers was 99%. The product poly(1-decene), after hydrogenation had a viscosity index of 138 and a pour point of <−45° C.

EXAMPLE 3

100 mL of freshly distilled 1-decene (<50 ppm moisture) was taken in a 250 mL three neck round bottom flask. The flask was equipped with a magnetic stirrer, nitrogen inlet and outlet and a condenser assembly. Silica supported catalyst, 4 g containing 5 wt. % of aluminum chloride and 30 wt. %. of diethylaluminum chloride was introduced into the flask. The contents were heated to 100° C. Oligomerization was carried out for 15 minutes. The product was filtered through a column of adsorbent alumina. The product composition was 15% dimer, 12% trimer, 17% tetramer, 16% pentamer and 40% hexamer. The % conversion of 1-decene to oligomers was 99%. The product poly(1-decene), after hydrogenation, had a viscosity index of 139 and pour point of −45° C.

EXAMPLE 4

An olefin-paraffin feed from refinery, typically, containing 20 wt. % alpha olefins in the carbon number range of $C_9$ to $C_{13}$, 2 wt. % internal olefins and balance 78 wt. % saturated hydrocarbons having the same range of carbon numbers was dried to <50 ppm moisture.

500 mL of this feed was taken in a one liter four neck round bottom flask. The flask was equipped with a magnetic stirrer, nitrogen inlet and outlet and a condenser assembly. Silica supported catalyst, 6 g containing 5 wt. % of aluminum chloride and 30 wt. % of diethylaluminum chloride, was introduced into the flask. The contents were heated to 120° C. Oligomerization was carried out for 30 minutes. The product was filtered through a column of adsorbent alumina and the paraffin distilled out at 160° C. under 50–60 mm Hg pressure. The product composition was 25% dimer, 41% trimer, 17% tetramer and 17% pentamer. The % conversion of olefins to oligomers was 99%. The product polyalpha-olefins, after hydrogenation had viscosity index of 138 and pour point of <−45° C.

EXAMPLE 5

An olefin-paraffin feed from refinery, typically containing 20 wt. % alpha olefins in the carbon number range of $C_9$ to $C_{13}$, 2 wt. % internal olefins and balance 78 wt. % saturated hydrocarbons having the same range of carbon numbers was dried to <50 ppm moisture.

500 mL of this feed was taken in a one liter four neck round bottom flask. The flask was equipped with a magnetic stirrer, nitrogen inlet and outlet and a condenser assembly. The feed was heated to 100° C. and 1.8 g of diethylaluminum chloride dissolved in about 10 mL of n-hexane was introduced into the flask. The contents were further heated to 150° C. Silica supported catalyst, 6 g containing 5 wt. % of aluminum chloride was introduced into the flask. Oligomerization was carried out for 12 minutes. The product was filtered through a column of adsorbent alumina and the solvent distilled out at 160° C. under 50–60 mm Hg pressure. The product composition was 37% dimer, 46% trimer, 14% tetramer and 3% pentamer. The 9% conversion of olefins to oligomers was 99%. The product polyalpha-olefins after hydrogenation had a viscosity index of 141 and pour point <−45° C.

EXAMPLE 6

10 mL of 1-decene, freshly distilled, was taken in a 50 mL round bottom flask equipped with a magnetic stirrer, nitrogen inlet and outlet and a condenser assembly. The flask was heated in an oil bath to 100° C. and diethylaluminum chloride, 0.12 g, diluted with about 1 mL of n-hexane and silica supported catalyst, 0.4 g containing 5 wt. % of aluminum chloride were introduced into the reaction flask. The oligomerization reaction was carried out for 30 minutes and the reaction mixture was allowed to cool. The solid catalyst was allowed to settle at the bottom of the flask and the supernatant product was removed using a syringe. Another aliquot of diethylaluminum chloride, 0.12 g dissolved in about 1 mL of n-hexane, was now introduced into the reaction flask, followed by 10 mL of 1-decene. The oligomerization run was repeated three times and the conversion was >99% in each run.

EXAMPLE 7

10 mL of 1-decene, freshly distilled, was taken in a 50 mL round bottom flask equipped with a magnetic stirrer, nitrogen inlet and outlet and a condenser assembly. The flask was heated in an oil bath to 100° C. and diethylaluminum chloride, 0.12 g, diluted with about 1 mL of n-hexane and silica supported catalyst, 0.4 g containing 5 wt. % of aluminum chloride were introduced into the reaction flask. The oligomerization reaction was carried out for 30 minutes and the reaction mixture was allowed to cool. The solid catalyst was allowed to settle at the bottom of the flask and the supernatant product was removed using a syringe. 10 mL of 1-decene was now introduced into the flask and oligomerization carried out for 30 minutes, without adding additional amounts of diethyl aluminum chloride. Three such runs were carried out and the conversions were 99%, 45% and 0% in the 1st, 2nd and 3rd runs respectively.

The significant advantages of the present invention are(a) use of supported solid catalyst which can be more conveniently handled than anhydrous aluminum chloride. Anhydrous aluminum chloride reacts violently with atmospheric moisture releasing fumes of corrosive hydrogen chloride gas (b) ability to reuse the catalyst repeatedly (c) reduced disposal and sludge handling problems and (d) ability to use a fixed bed reactor enabling continuous operation.

We claim:

1. A process for oligomerization and co-oligomerization of alpha olefins, comprising contacting feed alpha olefins having the general formula $C_nH_{2n}$, where n is an integer ranging from 6 to 20, with a supported catalyst containing aluminum chloride and an organoaluminum compound at a pressure ranging from 0 to 2 bars under oligomerization conditions to form a reaction product comprising poly alpha-olefins, and recovering said poly alpha-olefins.

2. A process as claimed in claim 1 wherein the step of oligomerization is carried out in the presence of saturated hydrocarbon solvent, which process further comprises a step wherein said solvent is removed from the reaction product by fractional distillation.

3. A process as claimed in claim 1 wherein the step of oligomerization is carried out in the absence of a solvent.

4. A process as claimed in claim 1 wherein the step of oligomerization is carried out a temperature of 125–175° C.

5. A process as claimed in claim 1 wherein the step of oligomerization is carried out for a period of 20 to 30 minutes.

6. A process as claimed in claim 1 wherein the organoaluminum compound has the general formula $AlR_nX_{3-n}$ where R is a linear or branched alkyl group with carbon number 1 to 10, X is a halogen, and n is a value ranging from 0.5 to 2.

7. A process as claimed in claim 1 wherein during the oligomerization step the alpha olefins are agitated with said catalyst in a stirred tank reactor.

8. A process as claimed in claim 1 wherein the catalyst is packed in a fixed bed and during the oligomerization step the alpha olefin reactants are fed over said bed.

9. The process of claim 1, which process further comprises fractionating the oligomers of said reaction product to obtain said poly alpha-olefins.

10. The process of claim 1, wherein the step of oligomerization is carried out at a temperature in the range of 60 to 180° C.

11. The process of claim 1, wherein the step of oligomerization is carried out so as to give an oligomerization reaction time of 10 minutes to 3 hours.

12. The process of claim 1, wherein the step of oligomerization is followed by a step wherein the catalyst is separated from the reaction product by filtration.

13. A process as claimed in claim 12 wherein the step of filtration is carried out in a column of adsorbent alumina.

* * * * *